United States Patent [19]
Golz-Berner et al.

[11] Patent Number: 6,036,969
[45] Date of Patent: Mar. 14, 2000

[54] PROCESS FOR MEASURING COSMETIC TANNING AND TEST KIT THEREFOR

[75] Inventors: Karin Golz-Berner; Leonhard Zastrow, both of Monaco, Monaco

[73] Assignee: Coty B. V., Haarlem, Netherlands

[21] Appl. No.: 09/362,460

[22] Filed: Jul. 28, 1999

[30] Foreign Application Priority Data

Jul. 29, 1998 [DE] Germany .......................... 198 34 938

[51] Int. Cl.[7] .............. A61K 7/00; A61K 7/42; B65D 67/00
[52] U.S. Cl. .......... 424/401; 206/223; 206/569; 424/1.69; 424/59; 424/60; 424/400
[58] Field of Search .................. 424/401, 400, 424/59, 60, 1.69; 206/223, 569

[56] References Cited

U.S. PATENT DOCUMENTS 5,705,145  1/1998  Miklean ..................................... 424/59

FOREIGN PATENT DOCUMENTS

WO 95/15742  6/1995  WIPO .

*Primary Examiner*—Shelley A. Dodson
*Attorney, Agent, or Firm*—Collard & Roe, P.C.

[57] ABSTRACT

There are a process for evaluating beforehand a self-tanning composition in reference to different skin types, and a test kit to implement the process. A cosmetic self-tanning medium containing dihydroxyacetone is thinly rubbed on at least one test field, and the resulting tan on the test field is visually evaluated after 5 seconds to 5 minutes. The test field has at least one substance selected from the group of amino acids Gly, Ala, Val, Leu, Ile, Ser, Thr, Cys, Met, Asn, Lys, Asp, Gln, Glu, Phe, Tyr, Trp, His, Pro and the purines adenine, guanine, xanthine and hypoxanthine and mixtures of individual compounds of these chemicals.

16 Claims, No Drawings

PROCESS FOR MEASURING COSMETIC TANNING AND TEST KIT THEREFOR

BACKGROUND OF THE INVENTION

1. Field of the Invention

The invention concerns a procedure to preevaluate a self-tanning medium in reference to different skin types, and a test kit to carry out the procedure.

2. The Prior Art

There are numerous prior-art self-tanning compositions on the market that contain dihydroxyacetone (1,3-dihydroxypropan-2-one, termed DHA in the following) as the essential tanning component at various concentrations and mixtures with other components. Depending on the additives in these cosmetic compositions and the concentration of the DHA, different tones are attained on human skin. These tones also depend on the respective skin type, or stated simply, white, brown or black skin.

A problem is that users have a difficult time determining which of the many offered self-tanning media will produce a specific tone from the numerous self-tanning compositions unless they pretest it on their skin and always use the same product with the same composition.

SUMMARY OF THE INVENTION

The invention is based on the problem of developing a process that can be used to largely predetermine the tan that will be created on human skin by a cosmetic self-tanning composition without prior skin contact.

Another problem of the invention is to offer a test set that can determine the skin coloration of the self-tanning medium depending on the skin color of the user.

According to the invention, the process to cosmetically predetermine the tan of a self-tanning composition on human skin consist of thinly rubbing the dihydroxyacetone-containing cosmetic self-tanning medium onto at least one test field on a substrate of paper or a film or plate of natural or synthetic materials. After 5 sec. to 5 min., the tan in the test field is visually evaluated.

The test field contains at least one substance that is selected from the group of amino acids Gly, Ala, Val, Leu, Ile, Ser, Thr, Cys, Met, Asn, Lys, Asp, Gln, Glu, Phe, Tyr, Trp, His, Pro and the purines adenine, guanine, xanthine and hypoxanthine and mixtures of individual compounds of these chemicals.

Preferred amino acids are those with a basic and hydrophilic side chain such as histidine, arginine and lysine in their L form.

A preferred purine is adenine (6-aminopurine).

A preferred embodiment of the process is to apply DHA-containing self-tanning medium to two test fields, one of which is pretreated with histidine, and the other is pretreated with adenine. After the self-tanning medium is applied, it is dried, e.g. at 20–50° C., and preferably at 20–40° C.

The concentration of amino acids and purine is generally 0.01–1.5 weight percent. When the concentration is under 0.01 weight percent, the tanning reaction is too weak. Concentrations above 1.5 weight percent produce tans that are too dark and unsuitable for the invention. Preferred concentration ranges for the substances are 0.05–0.9 weight percent.

The purity of the used substances is generally pharmaceutical purity, i.e., >99%.

After the self-tanning medium containing DHA is applied by painting or spraying a slight test amount on the test field, a tan color forms on the treated test surface generally within a few seconds, preferably 10–30 seconds. This tan is stable over a long period (hours to days), and can preferably be evaluated visually, or as desired with a corresponding optical instrument, and it can be compared with the users skin type and/or with a color scale.

A preferred embodiment of the invention is to mark two test fields with the substances: One test field e.g. with histidine for a dark skin type, and one test field with adenine for a light skin type. The tan that arises after the self-tanning, DHA-containing medium is applied then approximately corresponds to the tan that users with light or dark skin would attain after applying the self-tanning medium to their own skin.

Since the DHA concentrations in the commercially-available self-tanning media are different, the procedure according the invention helps the potential user of any DHA-containing product to previously determine the tone for his skin type that would result from using the product and then select the product.

In another embodiment of the invention, two or three adjacent test fields on a substrate are marked with the same substance, and the test fields are precolored with different tones that can correspond to skin color before tanning. The mixed tone produced after the DHA-containing self-tanning medium is applied then corresponds to the results for the respective skin type.

Instead of self-tanning media containing DHA, tanning media can be used that contain DHA precursors such as those in which the hydrogen of one or both OH groups is replaced by an alkoxycarbonyl group or arylalkyloxycarbonyl group, and the groups have 2–25 C atoms.

The process according to the invention can be carried out with conventional DHA-containing self-tanning media with different formulations. Normal formulations are cremes, sprays, gels, lotions and especially day cremes, sun-block cremes, body lotions, sun-block gels, and sun-block sprays.

Such preparations can contain other conventional cosmetic auxiliary mediums and carriers that are conventionally used in such preparations like water, preservatives, vitamins, dyes, free-radical scavengers, thickeners, softeners, moisturizers, perfumes, alcohols, polyols, electrolytes, gel forming agents, polar and nonpolar oils, polymers, copolymers, emulsifiers, waxes, and stabilizers.

Furthermore, they can contain conventional water-soluble and/or oil-soluble UVA or UVB filters, and inorganic pigments based on metal oxides as sun blocks.

The invention also concerns a test combination (termed test kit in the following) for self-tanning media based on dihydroxyacetone, characterized by:

a substrate material consisting of paper or another film or plate made of natural or synthetic materials;

a field marked on the substrate to which the substance is applied that is selected from the group of amino acids consisting of Gly, Ala, Val, Leu, Ile, Ser Thr, Cys, Met, Asn, Lys, Asp, Gln, Glu, Phe, Tyr, Trp, His, Pro and the purines adenine, guanine, xanthine and hypoxanthine and mixtures of individual compounds of these chemicals, and that react with the dihydroxyacetone or precursors of dihydroxyacetone in the self-tanning medium to form a tan.

Conventional test strip materials can be used for the substrate material. This includes different papers, films (e.g., as per DE 1598153) or open films (e.g. as per DE 2910134) that can be applied to a substrate such as a film, paper, glass, metal, plastic plates, etc. The above-cited films can be made of film formers such as polyvinyl esters, polyphenyl acetals, polyacrylic esters, polymethacrylic acid, polyacrylamides, polyamides, polystyrene, styrene-butadiene mixture polymers, and other film formers of natural and synthetic organic polymers that are preferably used as aqueous dispersions.

Absorbent paper can also be used as the substrate since problems that are to be expected from quantitative tests due to paper inhomogeneities do not arise in this form in the test according to the invention.

With the invention, a test paper can be used to select the skin type of the user from e.g. three marked fields such as light, medium and dark, and a thin coat of selected self-tanning medium can e.g. be lightly rubbed or sprayed onto the relevant test field. After the reaction time, the color is compared either with one's own skin or an accompanying color scale.

In one particularly advantageous embodiment of the test kit according to the invention, a sample of self-tanning medium is combined with a substrate that has marked test fields. The sample can come in conventional, flat, elastic, oil-tight and water-tight sealed sample containers, e.g. consisting of laminated aluminum foil, plastic film, etc. In this manner, e.g. samples of self-tanning medium can be offered with different DHA combinations, tested for expected skin tan, and selected in this manner by the user according to the desired tan.

In another embodiment of the test kit according to the invention, a color comparison scale for different tanning stages is placed next to one or more test fields.

The test field or fields can also be covered with a transparent or invisible film that is removed before use. It is not necessary to use such a film since normally the test field does not have to be additionally protected. The substance applied to the test field is normally wipe-resistant, and a color change only occurs when DHA is present on the field.

The invention will be further explained using examples. All figures are given in weight percent if not otherwise indicated.

DETAILED DESCRIPTION OF PREFERRED EMBODIMENTS

EXAMPLE 1

A conventional self-tanning composition was used containing 5.0 weight percent DHA.

An aqueous solution of 0.2 weight percent adenine was evenly sprayed on an open substrate film consisting of polyvinyl propionate/cellulose with $TiO_2$ components and dried in a drying cabinet at 40° C.

An aqueous solution of 0.2 weight percent L-histidine is evenly sprayed on another substrate film and dried in a drying cabinet at 40° C.

Pieces approximately 2 $cm^2$ were cut from both substrate films and applied to a paper base (intaglio paper) as a marked test surface I (adenine) and II (histidine).

The used self-tanning medium was thinly applied to the two marked surfaces with a finger. The two surfaces assumed different tans over 10 seconds. Test surface I showed a lighter tan and corresponded to the result of the skin tanning of the DHA self-tanning medium when applied to light skin. Test surface II contrastingly showed a dark tan and corresponded to the result of skin tan of the DHA self-tanning medium when applied to dark skin.

What is claimed is:

1. A process for cosmetically determining the tan of a self-tanning composition comprising the steps of thinly rubbing a cosmetic self-tanning medium containing dihydroxyacetone on at least one test field that is on a substrate selected from the group consisting of paper, a film, and a plate made of a material selected from the group consisting of natural material and synthetic material; and visually evaluating the resulting tan on the test field after 5 seconds to 5 minutes;

whereby the test field has at least one substance selected from the group consisting of amino acids Gly, Ala, Val, Leu, Ile, Ser, Thr, Cys, Met, Asn, Lys, Asp, Gln, Glu, Phe, Tyr, Trp, His, Pro and the purines adenine, guanine, xanthine and hypoxanthine and mixtures of individual compounds of these chemicals.

2. A process according to claim 1, comprising using a self-tanning composition that contains 0.5–7 weight percent dihydroxyacetone.

3. A process according to claim 1, comprising applying histidine to the test field.

4. A process according to claim 1, comprising applying arginine to the test field.

5. A process according to claim 1, comprising applying adenine to the test field.

6. A process according to claim 1, comprising visually evaluating the tan that results in the test field.

7. A process according to claim 1, comprising comparing the tan that results in the test field with a given comparative scale.

8. A process according to claim 1, comprising applying the substance at a concentration of 0.01–1.5 weight percent and then drying the substance.

9. A process according to claim 1, comprising using a self-tanning composition with a precursor of dihydroxyacetone in which the hydrogen of one or both OH groups is replaced by an alkoxycarbonyl group or arylalkyloxycarbonyl group, and each group has 2–25 carbon atoms.

10. A cosmetic test kit for a self-tanning medium based on dihydroxyacetone comprising a substrate material selected from the group consisting of paper, a film, and a plate made of a material selected from the group consisting of natural material and synthetic material;

a field marked on the substrate material to which a substance is applied that is selected from the group of amino acids consisting of Gly, Ala, Val, Leu, Ile, Ser, Thr, Cys, Met, Asn, Lys, Asp, Gln, Glu, Phe, Tyr, Trp, His, Pro and the purines adenine, guanine, xanthine and hypoxanthine and mixtures of individual compounds of these chemicals; and the self-tanning medium containing dihydroxyacetone or a precursor of dihydroxyacetone which reacts to form a tan.

11. A test kit according to claim 10, comprising two fields marked on the substrate material that have different substances selected from the group consisting of amino acids, purines, and from mixtures thereof.

12. A test kit according to claim 11, wherein one field contains adenine and a second field contains histidine.

13. A test kit according to claim 10, comprising three fields marked on the substrate that contain different substances selected from the group consisting of amino acids, purines, and mixtures thereof.

14. A test kit according to claim 11, wherein the fields also have different tones.

15. A test kit according to claim 10, further comprising a color comparison scale next to the substrate or next to the substrate with different skin tones.

16. A test kit according to claim 10, further comprising a removable film covering the test field.

* * * * *